US010564340B2

(12) United States Patent
Peng

(10) Patent No.: US 10,564,340 B2
(45) Date of Patent: Feb. 18, 2020

(54) MULTISPECTRAL LIGHT SOURCE DEVICE

(71) Applicant: Apacer Technology Inc., New Taipei (TW)

(72) Inventor: Chong-Jing Peng, New Taipei (TW)

(73) Assignee: APACER TECHNOLOGY INC., New Taipei (TW)

( * ) Notice: Subject to any disclaimer, the term of this patent is extended or adjusted under 35 U.S.C. 154(b) by 0 days.

(21) Appl. No.: 16/424,271

(22) Filed: May 28, 2019

(65) Prior Publication Data

US 2019/0369317 A1 Dec. 5, 2019

(30) Foreign Application Priority Data

Jun. 1, 2018 (TW) .............................. 107118863 A

(51) Int. Cl.
| | |
|---|---|
| *F21V 8/00* | (2006.01) |
| *F21V 3/00* | (2015.01) |
| *F21Y 113/17* | (2016.01) |
| *F21Y 115/10* | (2016.01) |

(52) U.S. Cl.
CPC .............. *G02B 6/0006* (2013.01); *F21V 3/00* (2013.01); *G02B 6/0008* (2013.01); *F21Y 2113/17* (2016.08); *F21Y 2115/10* (2016.08)

(58) Field of Classification Search
CPC . G02B 6/0006; G02B 6/0008; F21Y 2115/10; F21Y 2113/17; F21V 3/00
See application file for complete search history.

(56) References Cited

U.S. PATENT DOCUMENTS

| | | | |
|---|---|---|---|
| 8,724,054 B2 | 5/2014 | Jones | |
| 2010/0188018 A1* | 7/2010 | Salm | ......................... F21V 7/00 |
| | | | 315/294 |
| 2012/0212971 A1* | 8/2012 | Verbrugh | ............. G02B 6/0008 |
| | | | 362/552 |
| 2015/0043242 A1* | 2/2015 | Ding | .................. G03B 21/2033 |
| | | | 362/583 |
| 2016/0273716 A1 | 9/2016 | Tarsa et al. | |
| 2017/0315287 A1* | 11/2017 | Miyanaga | .............. C09K 11/00 |

\* cited by examiner

*Primary Examiner* — Kevin Quarterman
(74) *Attorney, Agent, or Firm* — Kirton McConkie; Evan R. Witt

(57) ABSTRACT

A multispectral light source device includes a substrate, a plurality of light-emitting diodes, a cover body and a light guide body. The light-emitting diodes are disposed on the substrate. A plurality of waveband lights with different wavelengths are emitted by the light-emitting diodes. The cover body is disposed on the substrate, and the light-emitting diodes are covered by the cover body. The light guide body is disposed on the substrate. The light guide body has a light guide outlet. The substrate has a first diameter, the light guide outlet has a second diameter, and the ratio of the first diameter to the second diameter is in a range between 9 to 15, so that the waveband lights are moved and converged in the light guide body and emitted through the light guide outlet. As a result, the product can be miniaturized, and the handheld detection instrument can be implemented.

10 Claims, 4 Drawing Sheets

MULTISPECTRAL LIGHT SOURCE DEVICE

CROSS-REFERENCE TO RELATED APPLICATION

This application claims priority from Taiwan Patent Application No. 107118863, filed on Jun. 1, 2018, the entire contents of which are incorporated herein by reference for all purposes.

FIELD OF THE INVENTION

The present invention relates to a light source device, and more particularly to a multispectral light source device.

BACKGROUND OF THE INVENTION

As a light source, a light-emitting diode is widely used in various types of detecting instruments, such as skin condition detecting devices, because of its features of stable light emission and low power consumption. In general, when using a light source device for detection, the light is usually emitted to the to-be-detected surface, and the reflected light is detected to obtain information.

When detecting waveband lights with different wavelengths, the light source device is often configured with a plurality of light-emitting diodes capable of emitting lights with different wavelengths, and is configured to emit light to the to-be-detected surface according to the optical path design to perform detection.

However, the light has the characteristics of scattering and reflecting. When the scattered light or reflected light of different light falls within the detection range, the detection result is abnormal and it is difficult to complete the detection. In addition, in order to match the optical path design of a plurality of light-emitting diodes, the product size of the light source device is inevitably difficult to reduce, and the purpose of the lightening and thinning of the detecting instrument cannot be achieved, and it is also difficult to design a hand-held detecting instrument.

Therefore, there is a need of providing an improved multispectral light source device distinct from the prior art in order to solve the above drawbacks.

SUMMARY OF THE INVENTION

Some embodiments of the present invention are to provide a multispectral light source device in order to overcome at least one of the above-mentioned drawbacks encountered by the prior arts.

The present invention provides a multispectral light source device. By the configuration of the light guide body and the substrate, and the combination of the plurality of light-emitting diodes, the integrated applications of the light-emitting diodes are implemented. A plurality of waveband lights are emitted from an extreme small substrate and then converged on a smaller light guide outlet. It can make the light-projecting position precise, make the detection environments the same, avoid the abnormal detection result caused by scattering or reflection, and then achieve the optimal detection. Meanwhile, the product can be miniaturized, and the handheld detection instrument can be implemented.

In accordance with an aspect of the present invention, there is provided a multispectral light source device. The multispectral light source device includes a substrate, a plurality of light-emitting diodes, a cover body and a light guide body. The light-emitting diodes are disposed on the substrate. A plurality of waveband lights with different wavelengths are emitted by the light-emitting diodes. The cover body is disposed on the substrate. The light-emitting diodes are covered by the cover body. The light guide body is disposed on the substrate. The light guide body has a light guide outlet. The substrate has a first diameter, the light guide outlet has a second diameter, and the ratio of the first diameter to the second diameter is in a range between 9 to 15, so that the waveband lights are moved and converged in the light guide body and emitted through the light guide outlet.

In accordance with another aspect of the present invention, there is provided a multispectral light source device. The multispectral light source device includes a substrate, a plurality of light-emitting diodes, a cover body and a light guide body. The light-emitting diodes are disposed on the substrate. A plurality of waveband lights with different wavelengths are emitted by the light-emitting diodes. The cover body is disposed on the substrate. The light-emitting diodes are covered by the cover body. The light guide body is disposed on the substrate. The light guide body has a light guide outlet and a light guide plate. The light guide plate and the light guide outlet are respectively disposed on two opposite sides of the light guide body, and the substrate is disposed on the light guide plate. The light guide body has a length, the substrate has a first diameter, the light guide outlet has a second diameter, the ratio of the length to the first diameter is in a range between 2 to 5, and the ratio of the first diameter to the second diameter is in a range between 9 to 15, so that the waveband lights are moved and converged in the light guide body and emitted through the light guide outlet.

The above contents of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 2:
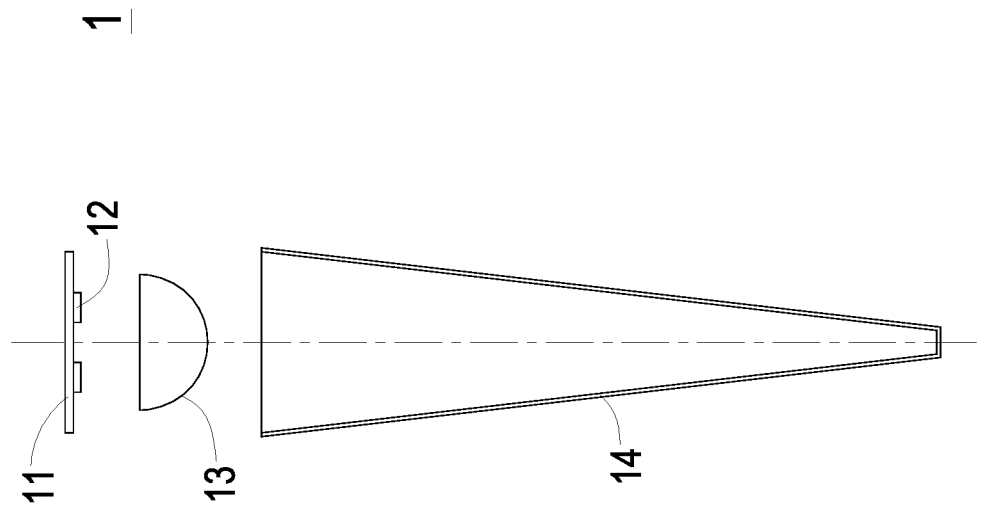
FIG. 2 schematically illustrates the sectional view of the exploded structure of the multispectral light source device shown in FIG. 1.
Figure 1:
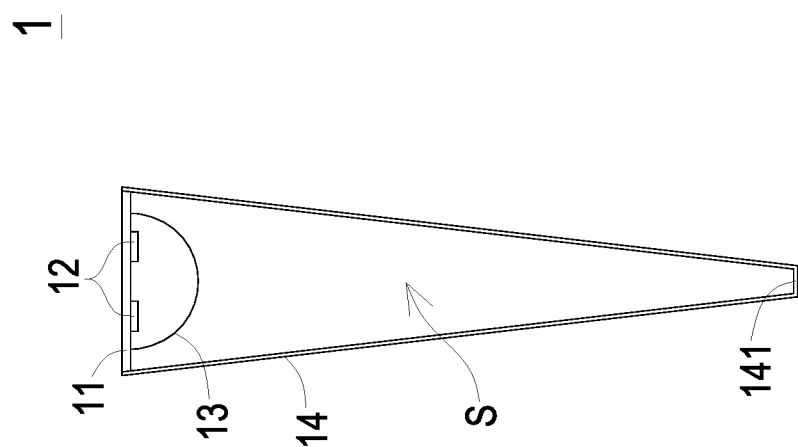
FIG. 1 schematically illustrates the sectional view of a multispectral light source device according to an embodiment of the present invention.
Figure 3B:
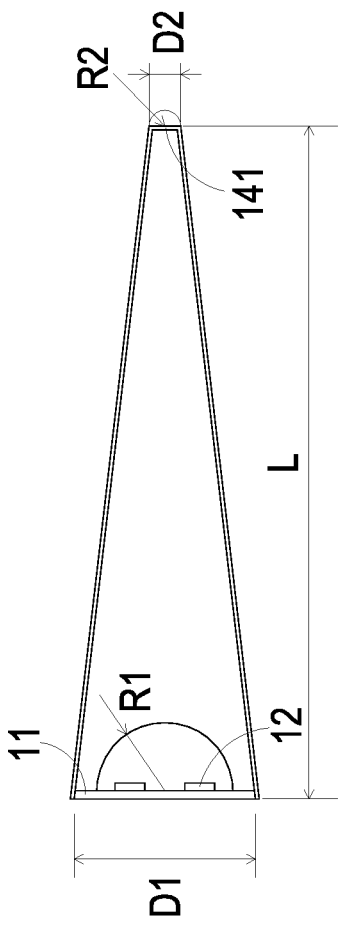
FIG. 3B schematically illustrates the size and specification of a multispectral light source device according to an embodiment of the present invention.
Figure 3A:
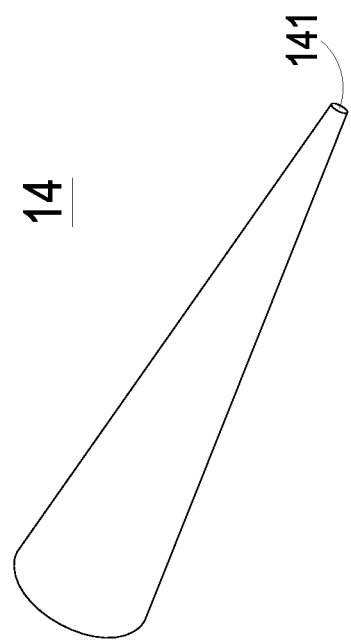
FIG. 3A schematically illustrates the structure of a light guide body of a multispectral light source device according to an embodiment of the present invention.

Please refer to FIG. 1, FIG. 2, FIG. 3A and FIG. 3B. FIG. 1 schematically illustrates the sectional view of a multispectral light source device according to an embodiment of the present invention. FIG. 2 schematically illustrates the sectional view of the exploded structure of the multispectral light source device shown in FIG. 1. FIG. 3A schematically illustrates the structure of a light guide body of a multispectral light source device according to an embodiment of the present invention. FIG. 3B schematically illustrates the size and specification of a multispectral light source device according to an embodiment of the present invention. As shown in FIGS. 1-3B, a multispectral light source device 1 according to an embodiment of the present invention includes a substrate 11, a plurality of light-emitting diodes 12, a cover body 13 and a light guide body 14. The light-emitting diodes 12 are disposed on the substrate 11. A plurality of waveband lights with different wavelengths are emitted by the light-emitting diodes 12. The waveband lights can each be visible light or invisible light. The cover body 13 is disposed on the substrate 11, and the light-emitting diodes 12 are covered by the cover body 13. The light guide body 14 is disposed on the substrate 11. The light guide body 14 has a light guide outlet 141. In this embodiment, the substrate 11 has a first diameter D1, the light guide outlet 141 has a second diameter D2, and the ratio of the first diameter D1 to the second diameter D2 is in a range between 9 to 15, so that the waveband lights are moved and converged in the light guide body 14 and emitted through the light guide outlet 141.

A part of the practical data is illustrated below to make the ratio range described above be easier to be understood. In some embodiments, the first diameter D1 of the substrate 11 can be 4 or 5 millimeters (mm), and the second diameter of the light guide outlet 141 can be 0.45 or 0.5 millimeters (mm), but not limited thereto. When the first diameter D1 is 5 mm and the second diameter D2 is 0.5 mm, the ratio of the first diameter D1 to the second diameter D2 is 10, which means that the multispectral light source device 1 of the present invention is able to make the waveband lights converge on the light guide outlet 141 with one-ten size. It can make the light-projecting position precise, make the detection environments the same.

In some embodiments, the substrate 11 of the multispectral light source device 1 of the present invention is preferred to be a circle-shaped substrate. The light guide body 14 is a tapered body, and the light guide body is preferred to be a truncated cone body. The light guide body 14 has a plurality of decreasing diameters different from each other from the substrate 11 to the light guiding outlet 141 in order to guide the light and make light be converged. In addition, the substrate 11 and the light guide body 14 are closed to form a light guide space S, and the substrate 11 and the light guide outlet 14 are respectively disposed on two opposite sides of the light guide space S. In specific, the substrate 11 and the light guide body 14 have exteriors and sizes corresponding to each other, and when the substrate 11 and the light guide body 14 are joined, they can be closely attached to each other, so that the light guide space S is formed. The waveband lights are moved in the light guide space S in manner of total reflection and emitted through and from the light guide outlet 141 by breaking the condition of total reflection at the light guide outlet 141.

Please refer to FIG. 3A and FIG. 3B again. In some embodiments, the light guide body 14 of the multispectral light source device 1 of the present invention has a length L, and the ratio of the length L to the first diameter D1 is in a range between 2 to 5. In other words, the length of the length L of the light guide body 14 is substantially 2 to 5 times of the length of the first diameter D1. That is, the relation between the first diameter D1 and the length L is written by D1:L=1:2 to D1:L=1:5. This range of the relation brings the best light guide efficiency. If the length L of the light guide body 14 is too long, it will cause the light decay phenomena. If the length L of the light guide body is too short, the light cannot be effectively guided, which causes poor light-emitting efficiency. Therefore, the ratio of the length L of the light guide body 14 of the multispectral light source device 1 to the first diameter D1 is preferably in the range between 2 to 5.

For example, when the first diameter D1 of the substrate 11 of the multispectral light source device 1 is 4 mm, the length L of the light guide body 14 can be 15 mm, and the ratio of the length L to the first diameter D1 is 3.75.

Please refer to FIG. 3B again. As shown in FIG. 3B, a cover body 13 of a multispectral light source device 1 according to an embodiment of the present invention is preferred to be a hemisphere. The cover body 13 has a first radius R1, and two times of the first radius R1 is less than the first diameter D1 of the substrate 11. On the other hand, the waveband lights are converged on the light guide outlet 141 to form a light point on the light guide outlet 141. The light point has a second radius R2, and the ratio of the first radius R1 to the second radius R2 is in a range between 7 to 10, but not limited thereto.

For example, when the first radius R1 of the cover body 13 of the multispectral light source device 1 is 2 mm, the second radius R2 of the light point formed on the light guide outlet 141 is 0.25 mm. The ratio of the first radius R1 to the second radius R2 is 8. That is, in the multispectral light source device 1, a plurality of waveband lights are emitted from an extreme small substrate 11 and then converged on a smaller light guide outlet 141. It can make the light-projecting position precise, make the detection environments the same, avoid the abnormal detection result caused by scattering or reflection, and then achieve the optimal detection. Meanwhile, the product can be miniaturized, and the handheld detection instrument can be implemented.

Figure 4:
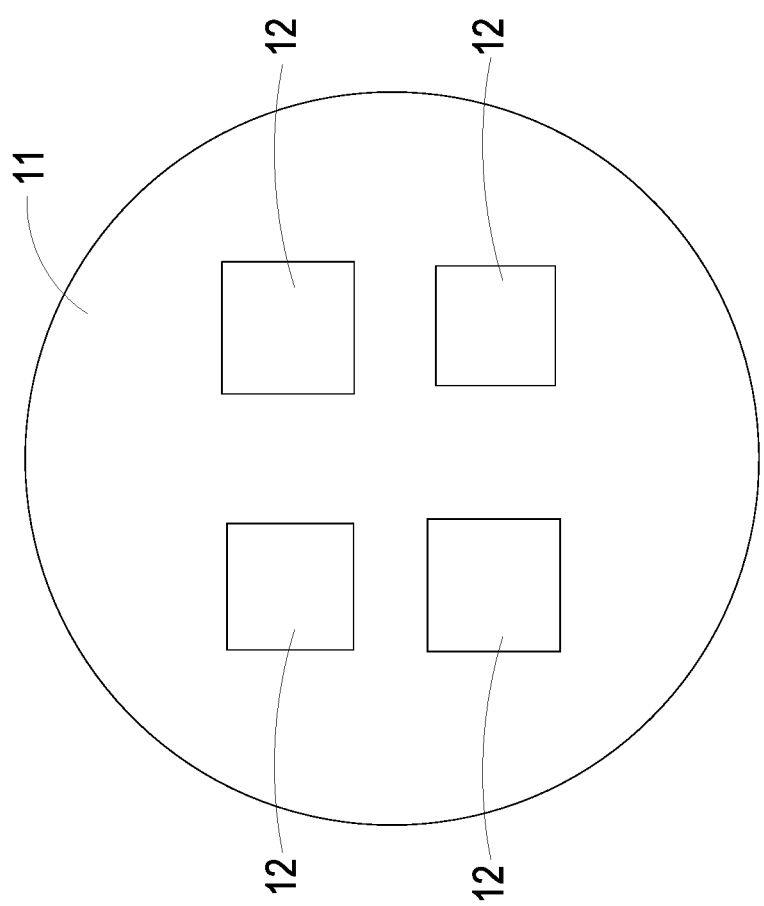
FIG. 4 schematically illustrates a plurality of light-emitting diodes disposed on a substrate.

Please refer to FIG. 1 and FIG. 4. FIG. 4 schematically illustrates a plurality of light-emitting diodes disposed on a substrate. As shown in FIG. 1 and FIG. 4, the number of the light-emitting diodes 12 of the multispectral light source device 1 is 3, 4, or 5, and is preferably 4, but not limited thereto. The light-emitting diodes 12 are all disposed on the substrate 11. In the application of the present invention, the multispectral light source device 1 is mainly applied to a detection instrument of skin condition. A peak value of wavelength of a waveband light having the maximum wavelength of the waveband lights, which are emitted by the plurality of the light-emitting diodes 12, is 905 nanometers. In this embodiment, four peak values of the four light-emitting diodes 12 are different from each other, so that they can be applied to detect different parameters, but not limited thereto.

Figure 6:
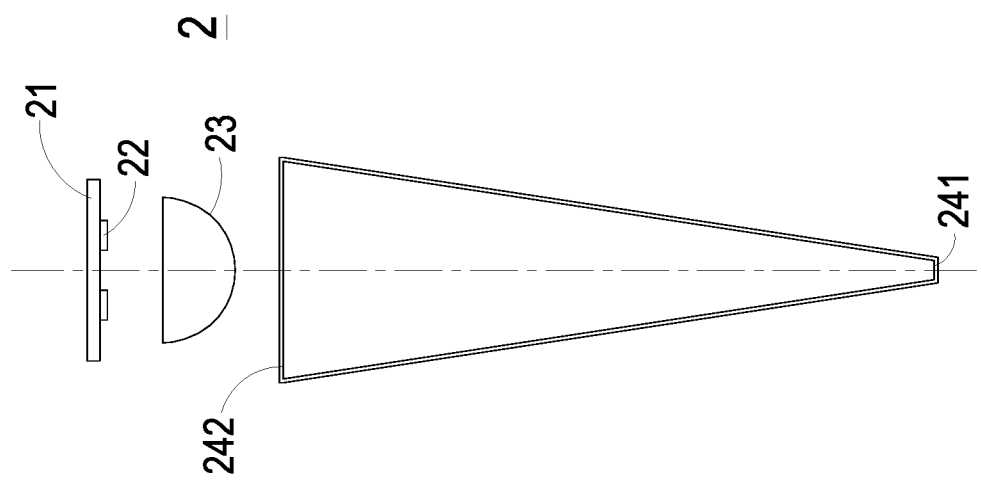
FIG. 6 schematically illustrates the sectional view of the exploded structure of the multispectral light source device shown in FIG. 5.
Figure 5:
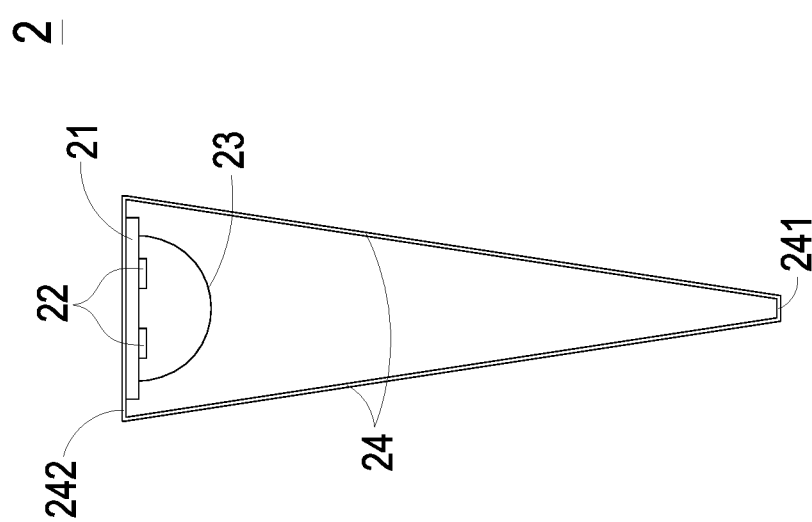
FIG. 5 schematically illustrates the sectional view of a multispectral light source device according to another embodiment of the present invention.

Please refer to FIG. 5 and FIG. 6. FIG. 5 schematically illustrates the sectional view of a multispectral light source device according to another embodiment of the present invention. FIG. 6 schematically illustrates the sectional view of the exploded structure of the multispectral light source device shown in FIG. 5. As shown in FIG. 5 and FIG. 6, a multispectral light source device 2 includes a substrate 21, a plurality of light-emitting diodes 22, a cover body 23 and a light guide body 24. The substrate 21, the light-emitting diodes 22 and the cover body 23 are similar with the substrate 11, the light-emitting diodes 12 and the cover body 13 of the multispectral light source device 1 described in the embodiments mentioned above, so it is not redundantly described herein. In this embodiment, the light guide body 24 of the multispectral light source device 2 has a light guide outlet 241 and a light guide plate 242. The light guide plate 242 and the light guide outlet 241 are respectively disposed on two opposite sides of the light guide body 24, and the substrate 21 is disposed on the light guide plate 242. In other words, the light guide body 24 may close itself to form a light guide space through the light guide outlet 241 and the light guide plate 242 of its own. There is no need to be adjusted or varied for matching with the size of the substrate 21, which is different from the substrate 11 and the light guide body 14 having the same exterior and size. Under this circumstance, the substrate 21 may have different exterior and shape from the light guide plate 242. The substrate 21 merely has to be selected to have the exterior and size which are able to be disposed on the light guide plate 242. The application diversity is enhanced. The light guide concept is as same as the embodiments mentioned above, so it is not redundantly described herein.

From the above discussion, the present invention provides a multispectral light source device. By the configuration of the light guide body and the substrate, and the combination of the plurality of light-emitting diodes, the integrated applications of the light-emitting diodes are implemented. A plurality of waveband lights are emitted from an extreme small substrate and then converged on a smaller light guide outlet. It can make the light-projecting position precise, make the detection environments the same, avoid the abnormal detection result caused by scattering or reflection, and then achieve the optimal detection. Meanwhile, the product can be miniaturized, and the handheld detection instrument can be implemented.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A multispectral light source device, comprising:
   a substrate;
   a plurality of light-emitting diodes disposed on the substrate, wherein a plurality of waveband lights with different wavelengths are emitted by the light-emitting diodes;
   a cover body disposed on the substrate, wherein the light-emitting diodes are covered by the cover body; and
   a light guide body disposed on the substrate, wherein the light guide body has a light guide outlet,
   wherein the substrate has a first diameter, the light guide outlet has a second diameter, and the ratio of the first diameter to the second diameter is in a range between 9 to 15, so that the waveband lights are moved and converged in the light guide body and emitted through the light guide outlet.

2. The multispectral light source device according to claim 1, wherein the substrate is a circle-shaped substrate, the light guide body is a tapered body, and the light guide body has a plurality of decreasing diameters different from each other from the substrate to the light guiding outlet.

3. The multispectral light source device according to claim 2, wherein the substrate and the light guide body are closed to form a light guide space, and the substrate and the light guide outlet are respectively disposed on two opposite sides of the light guide space.

4. The multispectral light source device according to claim 1, wherein the light guide body further has a light guide plate, the light guide plate and the light guide outlet are respectively disposed on two opposite sides of the light guide body, and the substrate is disposed on the light guide plate.

5. The multispectral light source device according to claim 1, wherein the number of the light-emitting diodes is 3, 4, or 5.

6. The multispectral light source device according to claim 1, wherein a peak value of wavelength of a waveband light having the maximum wavelength of the waveband lights is 905 nanometers.

7. The multispectral light source device according to claim 1, wherein the light guide body has a length, and the ratio of the length to the first diameter is in a range between 2 to 5.

8. The multispectral light source device according to claim 1, wherein the cover body is a hemisphere.

9. The multispectral light source device according to claim 8, wherein the waveband lights are converged on the light guide outlet to form a light point on the light guide outlet, the cover body has a first radius, the light point has a second radius, and the ratio of the first radius to the second radius is in a range between 7 to 10.

10. A multispectral light source device, comprising:
    a substrate;
    a plurality of light-emitting diodes disposed on the substrate, wherein a plurality of waveband lights with different wavelengths are emitted by the light-emitting diodes;
    a cover body disposed on the substrate, wherein the light-emitting diodes are covered by the cover body; and
    a light guide body disposed on the substrate, wherein the light guide body has a light guide outlet and a light guide plate, the light guide plate and the light guide outlet are respectively disposed on two opposite sides of the light guide body, and the substrate is disposed on the light guide plate,
    wherein the light guide body has a length, the substrate has a first diameter, the light guide outlet has a second diameter, the ratio of the length to the first diameter is in a range between 2 to 5, and the ratio of the first diameter to the second diameter is in a range between 9 to 15, so that the waveband lights are moved and converged in the light guide body and emitted through the light guide outlet.

\* \* \* \* \*